(12) United States Patent
Bennett et al.

(10) Patent No.: US 9,493,713 B2
(45) Date of Patent: Nov. 15, 2016

(54) SYSTEMS AND METHODS FOR CONDITIONING SYNTHETIC CRUDE OIL

(71) Applicant: Agilyx Corporation, Beaverton, OR (US)

(72) Inventors: James Michael Bennett, Gresham, OR (US); Kevin Clark DeWhitt, Vancouver, WA (US)

(73) Assignee: Agilyx Corporation, Beaverton, OR (US)

( * ) Notice: Subject to any disclaimer, the term of this patent is extended or adjusted under 35 U.S.C. 154(b) by 0 days.

(21) Appl. No.: 14/859,004

(22) Filed: Sep. 18, 2015

(65) Prior Publication Data

US 2016/0208177 A1 Jul. 21, 2016

Related U.S. Application Data

(63) Continuation of application No. 14/246,942, filed on Apr. 7, 2014, now Pat. No. 9,162,944.

(60) Provisional application No. 61/809,348, filed on Apr. 6, 2013.

(51) Int. Cl.
  *C07C 7/10* (2006.01)
  *C10G 53/12* (2006.01)

(52) U.S. Cl.
  CPC ..................... *C10G 53/12* (2013.01)

(58) Field of Classification Search
  None
  See application file for complete search history.

(56) References Cited

U.S. PATENT DOCUMENTS

| 1,153,141 | A | * | 9/1915 | Clark | ............... G03B 9/10 |
|---|---|---|---|---|---|
| | | | | | 396/494 |
| 1,553,141 | A | | 9/1925 | Clark | |
| 3,419,588 | A | | 12/1968 | de Man | |
| 3,810,563 | A | | 5/1974 | La Mers | |
| 4,164,484 | A | | 8/1979 | Tokuda et al. | |
| 4,168,942 | A | | 9/1979 | Firth | |
| 4,220,480 | A | | 9/1980 | Dwan | |
| 4,310,049 | A | | 1/1982 | Kalvinskas et al. | |
| 4,454,084 | A | | 6/1984 | Smith et al. | |
| 5,240,656 | A | | 8/1993 | Scheeres | |
| 5,269,947 | A | | 12/1993 | Baskis | |
| 5,321,174 | A | | 6/1994 | Evans et al. | |
| 5,342,421 | A | | 8/1994 | Breu | |
| 5,359,061 | A | | 10/1994 | Evans et al. | |
| 5,360,553 | A | | 11/1994 | Baskis | |

(Continued)

FOREIGN PATENT DOCUMENTS

| EP | 0 934 995 A1 | 8/1999 |
|---|---|---|
| GB | 2 231 057 A | 11/1990 |

(Continued)

OTHER PUBLICATIONS

Extended European Search Report, dated Nov. 25, 2013, for corresponding Application No. 10849161.4, 5 pages.

(Continued)

*Primary Examiner* — Tam M Nguyen
(74) *Attorney, Agent, or Firm* — Seed IP Law Group LLP

(57) ABSTRACT

Systems and methods for conditioning synthetic crude oils are provided herein. The systems and methods described herein subject the synthetic crude to one or more process solutions to provide conditioned synthetic crude exhibiting, for example, a reduced TAN.

13 Claims, 3 Drawing Sheets

(56) References Cited

U.S. PATENT DOCUMENTS

| | | |
|---|---|---|
| 5,427,650 A | 6/1995 | Holloway |
| 5,481,052 A | 1/1996 | Hardman et al. |
| 5,608,136 A | 3/1997 | Maezawa et al. |
| 5,623,863 A | 4/1997 | Plantan |
| 5,666,878 A | 9/1997 | Taricco |
| 5,731,483 A | 3/1998 | Stabel et al. |
| 5,744,668 A | 4/1998 | Zhou et al. |
| 5,780,696 A | 7/1998 | Bauer |
| 5,811,606 A | 9/1998 | Yang |
| 5,820,736 A | 10/1998 | Bouziane et al. |
| 5,821,396 A | 10/1998 | Bouziane |
| 5,824,193 A | 10/1998 | Edwards |
| 5,849,964 A | 12/1998 | Holighaus et al. |
| 5,973,217 A | 10/1999 | Hastrich et al. |
| 6,011,187 A | 1/2000 | Horizoe et al. |
| 6,046,370 A | 4/2000 | Affolter et al. |
| 6,060,631 A | 5/2000 | James, Jr. et al. |
| 6,150,577 A | 11/2000 | Miller et al. |
| 6,172,271 B1 | 1/2001 | Horizoe et al. |
| 6,190,542 B1 | 2/2001 | Comolli et al. |
| 6,288,296 B1 | 9/2001 | Miller et al. |
| 6,534,689 B1 | 3/2003 | Stankevitch |
| 6,861,568 B1 | 3/2005 | Guffey et al. |
| 7,626,062 B2 | 12/2009 | Carner |
| 7,758,729 B1 | 7/2010 | DeWhitt |
| 7,892,500 B2 | 2/2011 | Carner |
| 8,188,325 B2 | 5/2012 | DeWhitt |
| 8,192,586 B2 | 6/2012 | Garrison et al. |
| 8,192,587 B2 | 6/2012 | Garrison et al. |
| 8,193,403 B2 | 6/2012 | DeWhitt |
| 2002/0070104 A1 | 6/2002 | Nichols |
| 2002/0072640 A1 | 6/2002 | Nichols et al. |
| 2002/0156332 A1 | 10/2002 | Jiang |
| 2003/0047437 A1 | 3/2003 | Stankevitch |
| 2003/0050519 A1 | 3/2003 | Cheng |
| 2004/0050678 A1 | 3/2004 | Takahashi et al. |
| 2004/0222149 A1 | 11/2004 | Abrams |
| 2005/0075521 A1 | 4/2005 | Wada |
| 2005/0132883 A1 | 6/2005 | Su et al. |
| 2009/0036720 A1 | 2/2009 | Carner |
| 2009/0062581 A1 | 3/2009 | Appel et al. |
| 2011/0239541 A1 | 10/2011 | Garrison et al. |
| 2012/0034571 A1 | 2/2012 | Garrison et al. |
| 2012/0220675 A1* | 8/2012 | DeWhitt .............. C10B 47/18 521/40 |
| 2012/0222986 A1 | 9/2012 | Garrison et al. |

FOREIGN PATENT DOCUMENTS

| | | |
|---|---|---|
| JP | 10-88148 A | 4/1998 |
| JP | 10-219260 A | 8/1998 |
| JP | 11-158473 A | 6/1999 |
| JP | 2001-247874 A | 9/2001 |
| JP | 2003-073500 A | 3/2003 |
| JP | 2004-269755 A | 9/2004 |
| JP | 2007-229660 A | 9/2007 |
| JP | 2009-091387 A | 4/2009 |
| JP | 2010-121091 A | 6/2010 |
| WO | 2011/123145 A1 | 10/2011 |
| WO | 2011/123272 A1 | 10/2011 |

OTHER PUBLICATIONS

Heynderickx et al., "A Shell-and-Tube Pyrolysis Reactor for Olefin Production," *Ind. Eng. Chem. Res.* 31(9):2080-2087, 1992.

Interview Summary, mailed Jan. 20, 2012, for corresponding U.S. Appl. No. 13/273,089, 3 pages.

Interview Summary, mailed Jan. 20, 2012, for corresponding U.S. Appl. No. 13/273,097, 3 pages.

Interview Summary, mailed Jan. 23, 2012, for corresponding U.S. Appl. No. 12/751,911, 3 pages.

Japanese Office Action, dated Jul. 8, 2014, for corresponding Japanese Application No. 2013-502553, 7 pages. (English Translation).

Notice of Allowance, mailed Mar. 8, 2010, for corresponding U.S. Appl. No. 11/510,489, now U.S. Pat. No. 7,758,729, 18 pages.

Office Action, mailed Dec. 13, 2011, for U.S. Appl. No. 13/273,097, 7 pages.

Office Action, mailed Dec. 15, 2011, for corresponding U.S. Appl. No. 12/751,911, 8 pages.

Office Action, mailed Dec. 16, 2011, for U.S. Appl. No. 12/825,086, 10 pages.

Office Action, mailed Dec. 16, 2011, for U.S. Appl. No. 13/273,089, 8 pages.

Office Action, mailed Dec. 19, 2008, for corresponding U.S. Appl. No. 11/510,489, now U.S. Pat. No. 7,758,729, 12 pages.

Office Action, mailed Dec. 19, 2011, for U.S. Appl. No. 12/814,391, 9 pages.

Office Action, mailed Dec. 8, 2009, for corresponding U.S. Appl. No. 11/510,489, now U.S. Pat. No. 7,758,729, 12 pages.

Office Action, mailed Jul. 9, 2008, for corresponding U.S. Appl. No. 11/510,489, now U.S. Pat. No. 7,758,729, 6 pages.

PCT/US2014/033215, filed Apr. 7, 2014, International Search Report & Written Opinion, dated Aug. 25, 2014 (14 pgs).

Preliminary Amendment, filed Jun. 11, 2010, for corresponding U.S. Appl. No. 12/814,391, 3 pages.

Preliminary Amendment, filed Mar. 3, 2011, for corresponding U.S. Appl. No. 12/751,911, 15 pages.

Preliminary Amendment, filed Oct. 14, 2011, for corresponding U.S. Appl. No. 12/814,391, 9 pages.

Response to Office Action, filed Feb. 26, 2010, for corresponding U.S. Appl. No. 11/510,489, now U.S. Pat. No. 7,758,729, 9 pages.

Response to Office Action, filed Mar. 19, 2009, for corresponding U.S. Appl. No. 11/510,489, now U.S. Pat. No. 7,758,729, 9 pages.

Response to Office Action, filed Oct. 23, 2009, for corresponding U.S. Appl. No. 11/510,489, now U.S. Pat. No. 7,758,729, 9 pages.

Written Opinion of the International Searching Authority, mailed Apr. 28, 2011, for International Application No. PCT/US2010/040219, now WO 2011/123145, 5 pages.

Written Opinion of the International Searching Authority, mailed May 5, 2011, for International Application No. PCT/US2011/029129, now WO 2011/123272, 7 pages.

\* cited by examiner

SYSTEMS AND METHODS FOR CONDITIONING SYNTHETIC CRUDE OIL

TECHNICAL FIELD

The present disclosure relates generally to the conditioning of crude oils to reduce acid content and/or the presence of particulate and heteroatom contaminants. In certain embodiments, methods and systems for conditioning synthetic crude oils are provided.

BACKGROUND

Crude oils contain a complex mixture of different hydrocarbons of varying lengths and complexities. Crude oils also contain varying amounts of different contaminants, including, for example, organic acids and bases, inorganic acids and bases, metals, metalloids, and entrained particulates. Contaminants have potentially profound, deleterious impacts on refining processes and refinery equipment. As just one example, highly acidic crude oils lead to premature corrosion of refining equipment. The acidity of a crude oil is typically measured as the Total Acid Number (TAN), and it is generally desirable to reduce the TAN of a crude oil early in the refining process. In fact, because of the potential damage contaminated crude oils can cause, commercial refineries will reject crude oils exhibiting undesirably high levels of harmful contaminants, such as crude oils exhibiting high TAN values and/or crude oils containing high levels of certain metal, metalloid, or particulate species.

The nature and relative amounts of hydrocarbon components and the contaminant profile of crude oils vary tremendously, with crude oils derived from different materials, processes, and geographic locations exhibiting unique hydrocarbon and contaminant profiles. However, synthetic crude oils can exhibit particularly challenging contaminant profiles, often exhibiting high TAN values and including relatively high concentrations of one or more metal, metalloid, or particulate contaminants.

SUMMARY

Systems and methods for conditioning synthetic crude oils are provided herein. The systems and methods described herein subject the synthetic crude to a caustic wash by mixing the synthetic crude with an aqueous, caustic process solution (also referred to herein as a "caustic solution" or a "process solution"). By bringing the synthetic crude into intimate contact with the process solution, the systems and methods according to the present description provide conditioned synthetic crude exhibiting a reduced TAN.

Embodiments of the systems and methods described herein provide efficient conditioning of synthetic crude oil. Systems and methods according to the present description can quickly convert a crude oil product into a conditioned crude oil suited for commercial use or further refining, such as by any one of a number of commercial oil refining processes. Conditioned synthetic crude produced by systems and methods described herein may be readily stored and/or transported.

FIG. 1 provides a schematic illustration of conditioning system 100 for processing synthetic crude oil according to the present description. The conditioning system 100 includes synthetic crude delivery system 110, a process solution delivery system 120, a mixer 130, and a separator 140 for partitioning conditioned synthetic crude 150 from the process solution 160. The process solution delivery system 120 delivers the process solution to the mixer 130, and the synthetic crude is delivered to the mixer 130 by the synthetic crude delivery system 110. The synthetic crude and process solution are blended by the mixer 130 prior to delivery to the separator 140.

The separator 140 is configured to drive or facilitate separation of the synthetic crude from the process solution. The conditioned synthetic crude 150 may be removed from the separator 140 and delivered for storage, transportation, or for further on-site conditioning or refining. Process solution 160 may be drawn off from the separator 140 and disposed of or returned to the process solution delivery system 120 for continued utilization.

The conditioning system 100 optionally includes an oil filtration system (represented in FIG. 2). Filtering the crude oil, such as by microfiltration, removes entrained particulates. As a physical contaminant, entrained particles may cause fouling of refinery equipment. Moreover, the physical contamination resulting from entrained particulate materials may render the synthetic oil, whether crude or refined, unsuited to consumer or commercial applications. Beyond the problems created by physical contamination, however, particulate contaminants within the crude oil can create undesirable chemical characteristics. As one example, synthetic crude oils obtained from pyrolization of waste plastics may include particulate carbon black. Carbon black is not only a physical contaminant, but the inventors have found that contaminants adsorbed to or associated with carbon black can contribute to an undesirably high TAN.

Though the synthetic crude and process solution are generally immiscible, as they are blended by the mixer 130 and delivered to the separator 140, the synthetic crude and process solution may form an emulsion with an aqueous phase formed by the process solution (and any contaminants transferred into the process solution) and a hydrocarbon phase formed by the synthetic crude. Even where mixing of the process solution and synthetic crude results in an emulsion, the process solution and synthetic crude partition into two distinct phases in the separator 140. Therefore, in order to better ensure separation and recovery of the conditioned synthetic crude from the process solution, particular embodiments of the systems and methods described herein may be implemented to reduce or avoid saponification of hydrocarbons included in the synthetic crude. Additionally, embodiments of the systems and methods described herein may be implemented to avoid forming a stable emulsion as the synthetic crude and process solution are blended by the mixer 130 and delivered to the separator 140.

The systems and methods provided herein may be adapted to conditioning of a variety of synthetic crude oils obtained from various different hydrocarbon sources and by different production methods. For example, the systems described herein can be configured to provide two or more washing and separation steps. In such configurations, the systems may be configured to provide one or more initial washing and separation steps followed by a final washing and separation step adapted to provide a conditioned synthetic crude product having a desired TAN. In such embodiments, the one or more initial washing and separation steps may be targeted to remove or reduce contaminants that may not be affected by a caustic wash or do not contribute to the TAN of the synthetic crude. In certain embodiments, such contaminants may include, for example, particulates, metals, metalloids, and contaminants that may contribute to an undesirably high concentration of caustic species.

DETAILED DESCRIPTION

I. Definitions

Figure 1:
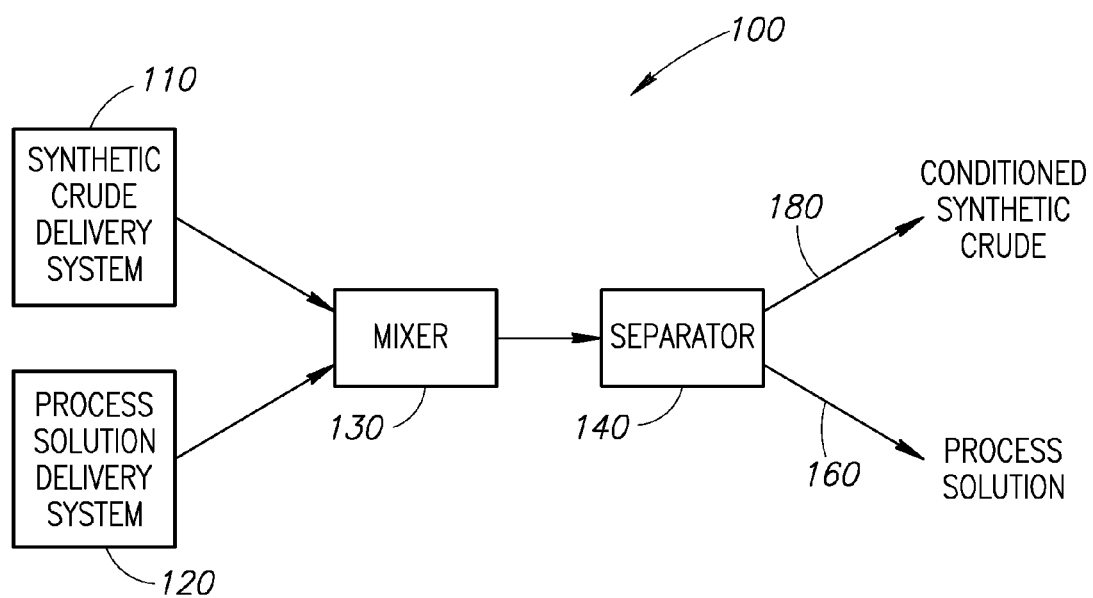
FIG. 1 provides a schematic illustration of an embodiment of synthetic crude oil conditioning system.

The term "contaminant" refers to any of a variety of impurities formed by heteroatoms, chemicals, particles, etc. present in a synthetic crude oil. Impurities can include, for example, inorganic acids (e.g., hydrochloric acid, hydrobromic acid), entrained metals or metalloids (e.g., cadmium, iron, antimony); entrained particles (e.g., carbon black); and/or organic acids (e.g., napthenic acids, terephthalic acid). In some embodiments, impurities found in the crude oil include polar organic molecules, such as one or more of various ketones, ethers, phenols, carboxylic acids, or other polar organic molecules. In other embodiments, impurities may include, for example, waste materials or impurities created by the presence of waste materials present in synthetic polymer materials used to product the synthetic crude.

The term "conditioning" refers to a process by which the concentration or presence of one or more contaminants contained in a synthetic crude oil is (are) reduced. The systems and methods described herein are suited to reducing one or more of, for example, the TAN, the concentration of metal and metalloid contaminants, and the concentration or presence of entrained particulates.

"Crude oil" and "crude oils" refer to condensed hydrocarbon products that include one or more contaminants in an amount that is higher than desired for commercially salable products or for refining of the crude oil in a commercial refining process.

References to "one embodiment," "an embodiment," or "the embodiment" mean that a particular feature, structure, system, step, or other characteristic described in connection with that embodiment is included in at least one embodiment. Thus, the quoted phrases, or variations thereof, as recited throughout this specification are not necessarily all referring to the same embodiment.

The term "heteroatom" generally refers to materials or molecular species that include atomic species other than carbon and hydrogen.

As used herein, "synthetic crude oil," "synthetic crude oils," and "synthetic crude" refer to crude oil obtained from oil shale, oil sands, and hydrocarbon-containing polymer materials, including synthetic polymer materials. Synthetic crude according to the present description may be obtained using a variety of processes. For example, in particular embodiments, synthetic crude may be obtained through shale oil pyrolysis. In other embodiments, synthetic crude may be obtained as an output from a bitumen/extra heavy oil upgrader facility used in connection with oil sand production. In still further embodiments, synthetic crude may be obtained by pyrolytic cracking of a polymer material followed by collection and condensation of the hydrocarbon species produced by pyrolysis. Synthetic crude oils processed by methods and systems as described herein may include, for example, one or more paraffins, olefins, naphthenes, aromatics, and/or other classes of hydrocarbon materials.

The terms "Total Acid Number" and "TAN" refer to total acidic constituents in a synthetic crude oil as measured using the ASTM D664 standard. This test method covers procedures for the determination of acidic constituents in petroleum products that are soluble or nearly soluble in mixtures of toluene and propan-2-ol. The range of TAN measured using the ASTM D664 standard is generally reported within a range of 0.1 mg/g KOH to 150 mg/g KOH. In particular embodiments, conditioned synthetic crude processed using the systems and methods provided herein exhibits a TAN of about 0.5 mg/g KOH or less. In certain such embodiments, the conditioned synthetic crude exhibits a TAN of about 0.3 mg/g KOH or less, and in still further such embodiments, the conditioned synthetic crude exhibits a TAN of about 0.1 mg/g KOH or less.

II. Systems for Conditioning Synthetic Crude Oil

The systems and methods provided herein are described in the context of synthetic crude obtained from pyrolysis of one or more synthetic polymer materials. Synthetic crude oils can be produced from synthetic plastic and rubber materials, including, for example, mixed plastic waste, rubber waste, and mixtures of plastic and rubber materials. Synthetic polymer materials processed to obtain a synthetic crude oil as described herein may be selected from, for example, tires, construction materials, packaging materials, and other polymer, plastic, and rubber materials used in consumer goods, medical devices, transportation industries, etc. Methods and systems for obtaining synthetic crude oil from pyrolysis of synthetic polymer material are known. Examples of methods and systems available for recycling synthetic polymer material, including waste materials, into a synthetic crude and are described, for instance, in U.S. Pat. No. 8,193,403, the entirety of which is herein incorporated by reference. Even though, the systems and methods provided herein are described in the context of synthetic crude obtained from pyrolysis of one or more synthetic polymer materials, it will be understood that the systems and methods are not so limited and may be applied to reduce the contaminant profile of synthetic crude oils obtained from different sources and by different methods.

Synthetic crude oils obtained from pyrolysis of synthetic polymers may exhibit a highly variable contaminant profiles. This is particularly true, where recycled polymer material is sourced from mixed waste plastic and/or rubber. Such materials can be, and often are, contaminated with water, foodstuffs, labeling materials, soil, paper, or cellulose waste. Moreover, recycled synthetic polymers often include internal amendments, such as glass, metal, iron, bromine, and/or chlorine. Even further, in the course of capturing and condensing hydrocarbons obtained from a pyrolytic process, fine particulate material, including particulate carbon black, may be drawn off and entrained within the synthetic crude product as the hydrocarbons generated from pyrolysis are condensed.

Systems for conditioning synthetic crude according to the present description are described in more detail with reference to FIG. 2 and FIG. 3. Though the systems provided herein are described with reference to FIG. 1 through FIG. 3, these figures are provided only to facilitate description. The systems taught herein are not limited to a specific configuration or the specific configurations illustrated in the accompanying figures. Systems according to the present description can be adapted to condition synthetic crude obtained from various sources by different processes, and the systems provided herein can be implemented in differing contexts. For example, in some embodiments, the conditioning system may be implemented as a stand-alone system where synthetic crude is delivered to the system, conditioned, and collected for storage, further processing, use, or sale. In other embodiments, the conditioning system may be integrated into a synthetic crude production process, with the synthetic crude being delivered directly to the conditioning system as output from a crude oil production process without intermediate storage or transportation steps.

Figure 2:
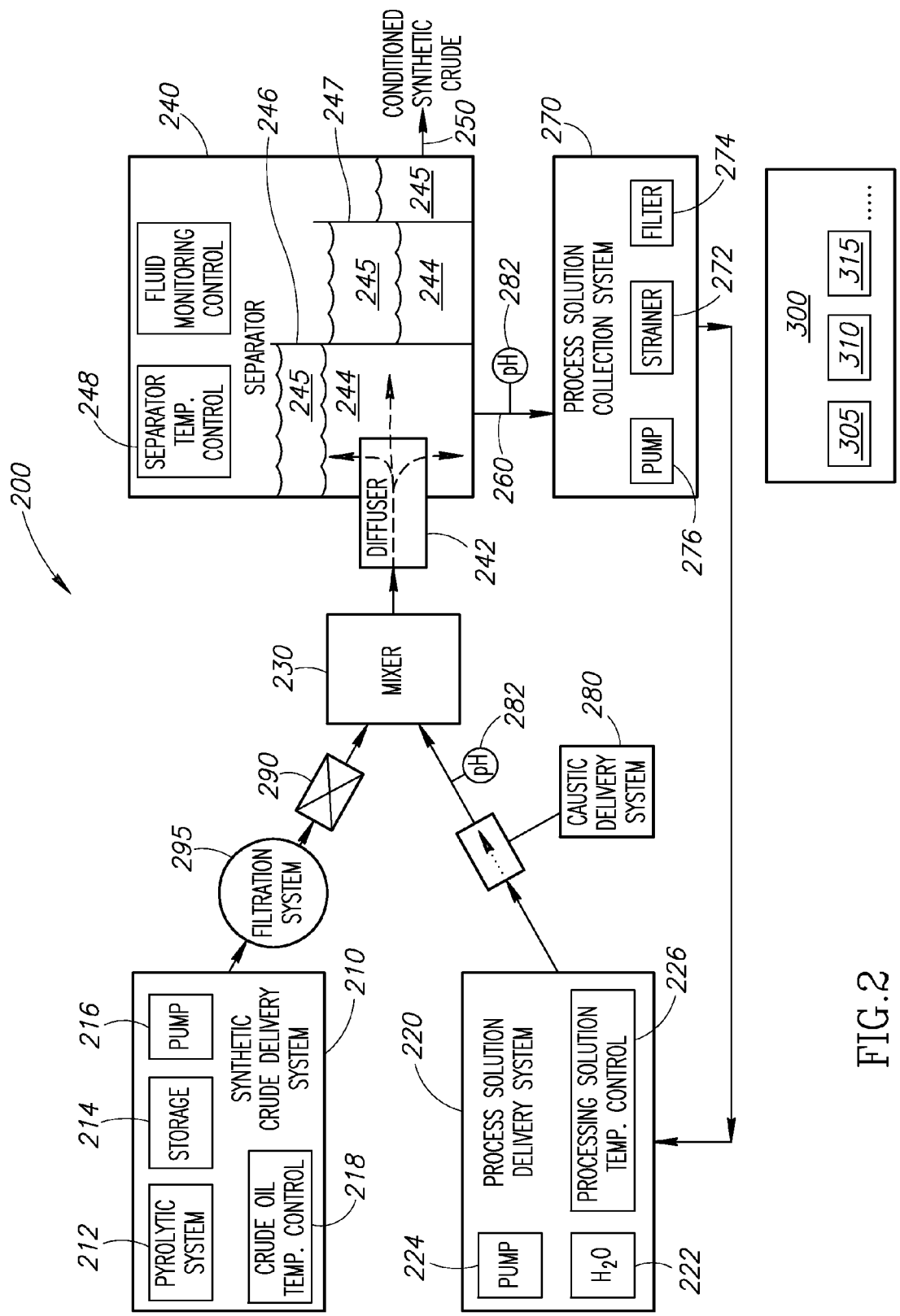
FIG. 2 provides a schematic illustration of another embodiment of a synthetic crude oil conditioning system.

FIG. 2 illustrates an embodiment of a conditioning system 200. The conditioning system 200 includes a synthetic crude delivery system 210, a process solution delivery system 220, a mixer 230, and a separator 240. In the embodiment illustrated in FIG. 2, the conditioning system 200 also includes a flow sensor 290 for measuring the amount of synthetic crude oil entering the mixer 230, a filtration system 295, a process solution collection system 270, and a master control system 300.

The synthetic crude delivery system 210 includes a source of synthetic crude for delivery to the mixer 230. The source of synthetic crude may depend on the context in which the conditioning system 200 is implemented. As illustrated in FIG. 2, the source of synthetic crude may include one or more of a storage tank 214 or a system for producing synthetic crude oil, such as a pyrolytic system 212 generating crude synthetic oil by pyrolysis of hydrocarbon containing materials. Though not illustrated in FIG. 2, the source of synthetic crude oil may also include another conditioning system or, where the synthetic crude may benefit from further conditioning, a return system that collects synthetic crude from the separator 240 and returns it to the synthetic crude delivery system 210. To deliver the synthetic crude to the mixer 230, the synthetic crude delivery system 210 may include one or more pumps 216. Pumps suitable for use in this context are commercially available and include, for example, gear-type pumps available from Maag Industrial Pumps and Tuthill Corporation. In alternative embodiments, the synthetic crude delivery system 210 may be configured to provide a motivating force by means other than one or more pumps 216, such as by the force of gravity.

The process solution delivery system 220 includes a water source 222 (for purposes of the present disclosure, "water" refers to any suitable aqueous carrier, including, for example, distilled water, filtered water, deionized water, and any other aqueous solvents capable of forming the process solution). The process solution delivery system 220 may also be configured to receive recycled process solution 260 delivered from a process solution collection system 270. The process solution delivery system 220 may also include one or more pumps 224 to deliver the process solution to the mixer 230. Pumps suitable for delivering the process solution are commercially available and include, for example, centrifugal-type pumps available from Sundyne (e.g., Ansimag pumps) and Flowserve Corporation (e.g., Innomag pumps).

The process solution is a caustic solution formed using one or more chemical amendments of any suitable variety to achieve the desired solution properties. Such properties may include, for example, high immiscibility with the synthetic crude oil and the ability to remove or neutralize one or more impurities. Adjustment of such properties may be achieved by altering the concentration of the one or more chemical amendments within the caustic process solution. For example, the presence, combination, and/or concentration of one or more materials within the caustic process solution can better facilitate removal of contaminants from the crude oil as it mixes and interacts with the caustic process solution.

As contemplated herein, a process solution is an alkaline aqueous solution exhibiting a pH of about 8 or above and can be prepared, for example, by dissolving a caustic amendment, such as a water soluble base, in an aqueous carrier. In particular embodiments, the process solution may be prepared using one or more bases selected from potassium hydroxide (KOH), calcium hydroxide ($Ca(OH)_2$), cesium hydroxide (CsOH), Barium hydroxide ($Ba(OH)_2$), sodium hydroxide (NaOH), strontium hydroxide ($Sr(OH)_2$), and lithium hydroxide (LiOH). The process solution may be buffered to maintain a desired pH. In specific embodiments, the pH of the process solution is above a pH of about 8 but not higher than a pH of about 10. For example, a caustic process solution may have a pH of between a pH of about 9 and a pH of about 10. The inventors have found that increasing the pH above a pH of about 10 may result in saponification of the crude oil and/or production of a stable emulsion as the synthetic crude and the process solution are mixed. The process solution may not only serve to reduce the TAN of the synthetic crude, but the caustic wash it provides may capture polar impurities, metals, or other impurities that have an affinity to or will partition into an alkaline solution.

In the embodiment illustrated in FIG. 2, the conditioning system 200 includes a caustic delivery system 280, and one or more pH sensors 282. Based on pH readings provided by the one or more pH sensors 282, the caustic delivery system 280 may be configured to adjust the amount of caustic material delivered to the process solution. For example, where the one or more pH sensors 282 indicate that the pH of the process solution is below about 8, the caustic delivery system may be configured to deliver sufficient caustic material to increase the pH to a targeted level (e.g., a pH of between about 8.0 and about 10, such as a pH of between about 9.0 and about 10, including a pH of about 9.5).

Synthetic crude oils obtained from different source materials will exhibit different TAN values. The process solution delivery system 220 and the conditioning system 200 are configured to be adaptable to conditioning of synthetic crude oils having widely ranging acid content. In order to achieve a desired TAN for a given synthetic crude, the volume of process solution delivered by the process solution delivery system 220 may be adjusted. By adjusting the volume of process solution delivered to the mixer 230, even synthetic crude oils exhibiting very high TAN values can be conditioned without using a process solution having a pH above about 10.

The system illustrated in FIG. 2 includes a flow rate monitor 290 that determines the volume of synthetic crude delivered to the mixer 230. Using the flow rate provided by the flow rate monitor 290, the volume of process solution delivered to the mixer can be adjusted to provide a desired reduction in TAN, while maintaining the pH of the process solution within a desired range as it is mixed with a given volume of synthetic crude. In particular embodiments, the conditioning system 200, including the synthetic crude delivery system 210, the process solution delivery system 220, and the caustic delivery system 280 are configured to adjust delivery of the process solution to a range of volume ratios. In such embodiments, the ratio of the volume of synthetic crude to the volume of process solution delivered to the mixer 230 may fall within a range selected from the group of ranges consisting of above about 1:1 to about 1:200, about 1:2 to about 1:200, about 1:3 to about 1:200, and about 1:4 to about 1:200. In further such embodiments, the ratio of the volume of synthetic crude to the volume of process solution delivered to the mixer 230 may be a range selected from the group of ranges consisting of about 1:2 to about 1:100, about 1:2 to about 1:50, about 1:2 to about 1:25, about 1:2 to about 1:10, and about 1:2 to about 1:5.

The synthetic crude and the processing solution are blended and brought into intimate contact by the mixer 230. In particular embodiments, the mixer 230 blends the synthetic crude and processing solution such that an emulsion is formed. The mixer 230 may utilize any suitable means or configuration to bring the process solution and synthetic crude into intimate contact. In certain embodiments, the mixer 230 may be configured to introduce the synthetic crude oil into the process solution through a bubbler or diffuser. In other embodiments, the mixer includes a low-shear static or kinetic mixer. In certain such embodiments, the conditioning system 200 may be configured such that mixing of the process solution and synthetic crude oil take place in-line.

In-line mixing of the process solution and crude oil may be accomplished, for example, by delivering the process solution and crude oil to the mixer 230 via a common conduit. In such an embodiment, the process solution may be delivered into a conduit carrying the synthetic crude oil or the synthetic crude oil may be delivered into a conduit carrying the process solution before entering the mixer 230. Alternatively, the conditioning system may be configured such that the synthetic crude and the process solution do not blend prior to being introduced into the mixer 230. In yet other embodiments, separate conduits carrying a process solution and the synthetic crude oil may be configured to deliver the process solution and crude oil to a third conduit, such as through a Y-shaped or divided T-shaped junction. Where mixing occurs in-line, the process solution and synthetic crude oil may be pumped or otherwise driven through (such as by the force of gravity) conduits carrying each of the synthetic crude oil, the process solution, and the mixture of the synthetic crude oil and process solution. Moreover, in specific embodiments, where mixing of the crude oil and process solution occur in-line, the mixing device used may be selected from one of a variety of commercially available static, in-line mixers. Static, in-line and low shear mixers are available from a number of suppliers including, for example, Koflo Corporation, JDMix, Inc.

Once the crude oil and the process solution have been mixed, they are delivered to a separator 240. The separator 240 may take on any configuration suitable to cause separation of the synthetic crude oil from the process solution. For example, the separator 240 may incorporate a centrifuge (not shown) that operates to separate the blended synthetic crude and process solution. In alternative embodiments, the separator 240 includes a separation tank 241 configured to facilitate partitioning of the process solution into a first phase 244 that is distinct from a second phase 245 formed by the synthetic crude. In one such embodiment, the separation tank 241 may include one or more weirs 246, 247 to facilitate continuous delivery of mixed synthetic crude oil and process solution, while also providing stepwise separation of the first and second liquid phases 244, 245 formed by the synthetic crude and the process solution.

In specific embodiments, where a separation tank 241 is used to separate the synthetic crude and process solution, the mixture of process solution and crude oil may be delivered to the separation tank 241 via a diffuser 242. In particular embodiments, the blended process solution and synthetic crude may be delivered into the separation tank via multiple conduits, with each conduit in fluid communication with one or more diffusers (not shown). Where included, a diffuser 242 may facilitate more rapid phase separation, as the diffuser can be selected and configured such that the process solution and synthetic crude constituents have different affinities for the diffuser or may exhibit different average residence times within the diffuser. Once the first and second phases 244, 245 are separated, the conditioned synthetic crude 260 is collected from the separation tank 241 and can be delivered for further conditioning, delivered to a storage tank, or delivered directly to a process for refining the conditioned synthetic crude 260.

The separated process solution 260 can be collected and recirculated for continued use by a process solution collection system 270. The process solution collection system 270 may include one or more pumps 276 configured to draw process solution out from the separator 240 and/or deliver the separated process solution 260 back to the process solution delivery system 220. Pumps suitable for use in the process solution collection system are commercially available and include, for example, centrifugal-type pumps available from Sundyne (e.g., Ansimag pumps) and Flowserve Corporation (e.g., Innomag pumps). The process solution collection system may be configured to pass the separated process solution through one or more strainers 272 and/or filters 274 to collect precipitates, agglomerates, or other particles that partition into or form within the process solution.

The conditioning system may also include a filtration system 295 for removing particulate contaminants from the synthetic crude before it is blended with the process solution. The filtration system 295 may be configured for microfiltration of the synthetic crude delivered by the synthetic crude delivery system 210. Microfiltration of the synthetic crude oil removes entrained particulate materials which can foul refining equipment, contribute to the TAN of the synthetic crude, or result in an unsalable refined product. In particular embodiments, among other particulates, the filtration system may be configured to remove fine, carbon black particulates entrained within the synthetic crude. Carbon black is not only a physical contaminant, but its presence can increase the TAN of the synthetic crude due to the presence of adsorbed acids or other associated impurities.

In specific embodiments, the filtration system 295 includes filter media capable of capturing entrained particles sized above about 500 µm in any dimension. For example, the filter media included in the filtration system 295 may be selected to capture particles sized above about 500 µm, 400 µm, 300 µm, 200 µm, 100 µm, 50 µm, 25 µm, 10 µm, and 5 µm in any dimension. In other embodiments, the filter media may be selected to capture particles sized at about 200 µm and above in any dimension. In still further embodiments, the filter media may be selected to capture particles sized at about 1 µm and above in any dimension. Any commercially available filter or filter media compatible with the selected synthetic crude oil and capable of capturing particles within the desired size range may be used for filtering the synthetic crude. In specific embodiments, the filter media includes one or more sintered metal filters, such as those available from Mott Corporation (http://www.mottcorp.com/).

The filtration system 295 may be configured to filter the synthetic crude in a single step. In such an embodiment, filtering of the synthetic crude oil may be accomplished by a single pass through a filter media or canister. However, in other embodiments, the filtration system may be configured to filter the synthetic crude over multiple or progressive filtering steps. In such embodiments, the synthetic crude oil may be passaged through two or more filters having the same porosity, better ensuring that all particulates within a certain size range are removed. As an alternative, or additionally, the synthetic crude oil may be subjected to passaging through multiple filters configured to capture progressively finer particulate material. Such an approach may be advantageous where the synthetic crude oil contains significant amounts of entrained particulates and those particulates exhibit a relatively wide particle size distribution. To filter the synthetic crude, a force drawing or driving the crude oil through the filter and filter media is needed. Such a force may be provided, for example, by capillary action, by gravity, or by pneumatic or hydraulic pressure exerted by commercially available pumps. Examples of pumps that may be utilized in the filtration system 295 include, for example, gear-type pumps available from Maag Industrial Pumps and Tuthill Corporation.

The components of a conditioning system 200 according to the present description, including the systems for delivering, mixing, separating, circulating, and collecting process solutions and synthetic crude oil may include any suitable combination of conduit, piping, flow switches and valves to allow for the desired amount of synthetic crude and process solution to be delivered, mixed, separated, and collected. In addition to those already described, conditioning systems according to the present description may also incorporate one or more commercially available flow sensors, pH sensors, pressure sensors, level sensors, etc. in operative communication with one or more monitoring and control systems.

The conditioning system 200 illustrated in FIG. 2 includes a master control system 300 configured to monitor and control operational parameters of the conditioning system 200. The master control system 300 may be configured and programmed to receive and process data from one or more of the synthetic crude oil delivery system 210, the process solution delivery system 220, the mixer 230, the separator 240, the process solution collection system 270, the filtration system 295, and the caustic delivery system 280 (referred to collectively as "system components"). In such an embodiment, the system components may include or be in operative communication with one or more sensors, such as a pH sensor, a flow rate sensor, a temperature sensor, a fluid level sensor, etc., and such sensors may collect and transmit process data to a system component controller 305, 310, 315 or directly to the master control system 300. The data can be processed and the master control system 300, either directly or through one or more system component controllers 305, 310, 315, may alter the operational parameters of the conditioning system 200 to provide a conditioned synthetic crude having a targeted TAN or contaminant profile.

In certain embodiments, the master control system 300 may be configured to communicate with one or more system component controllers 305, 310, 315 (e.g., via an Ethernet cable or other suitable communication device, whether wired or wireless), with each system component controller being dedicated to a particular system component of the conditioning system 200. For example, separate system component controllers 305, 310, 315 may be dedicated to one or more of the synthetic crude oil delivery system 210, the process solution delivery system 220, the mixer 230, the separator 240, the process solution collection system 270, the filtration system 295, and the caustic delivery system 280. In some embodiments, the system component controllers 305, 310, 315 are situated locally (e.g., near the various system components with which they are associated), whereas the master control system 300 may be situated in a supervisory station where an operator can monitor the instantaneous status of the multiple component systems and make changes thereto as desired, whether onsite or offsite.

The steps or control events discussed herein which can be effect a system component controller 305, 310, 315 and/or the master control system 300 may be embodied in machine-executable instructions that are to be executed by a general-purpose or special-purpose computer (or other electronic device). Alternatively, the steps or control events may be performed or instigated by hardware components that include specific logic for performing the steps or control events, or by a combination of hardware, software, and/or firmware. Some or all of the steps may be performed locally (e.g., via a subsystem controller) or remotely (e.g., via the master control system).

Crude oils of differing origins may exhibit different physical properties, including different viscosities at room temperature. Some synthetic crude oils may be highly viscous, semi-solid, or even solid materials at room temperature. Where such is the case, the process solutions, synthetic crude oil, and systems for delivering, filtering, mixing, separating, and collecting the process solutions and synthetic crude may be heated and/or maintained at an elevated temperature (e.g., a temperature selected from different ranges of temperatures including, for example, about 100° F. to about 200° F., about 125° F. to about 200° F., 1 about 50° F. to about 200° F., about 175° F. to about 200° F., about 100° F. to about 175° F., about 100° F. to about 150° F., about 100° F. to about 125° F., about 125° F. to about 175° F., and about 125° F. to about 150° F.) to ensure the synthetic crude oil remains in a liquid state as it is processed. Other crude oils, however, may be much more volatile, and, if needed, the conditioning systems described herein may include one or more cooling mechanisms to ensure the volatile crude oil is maintained in a liquid state as it is filtered, conditioned and collected.

To accomplish the desired temperature control, the conditioning system 200 may include one or more of a crude oil temperature control system 218, a processing solution temperature control system 226, and a separator temperature control system 248. The one or more temperature control systems 218, 226, 248 included in a conditioning system 200 may be configured to communicate with one or more system component controllers 305, 310, 315 or the master control system 300 (e.g., via an Ethernet cable or other suitable communication device, whether wired or wireless). In such an embodiment, the master control system 300 can be configured to enable control of the one or more temperature control systems 218, 226, 248 through a system component controller 305, 310, 315 based on information received from the temperature control systems 218, 226, 228 or their associated component system.

Figure 3:
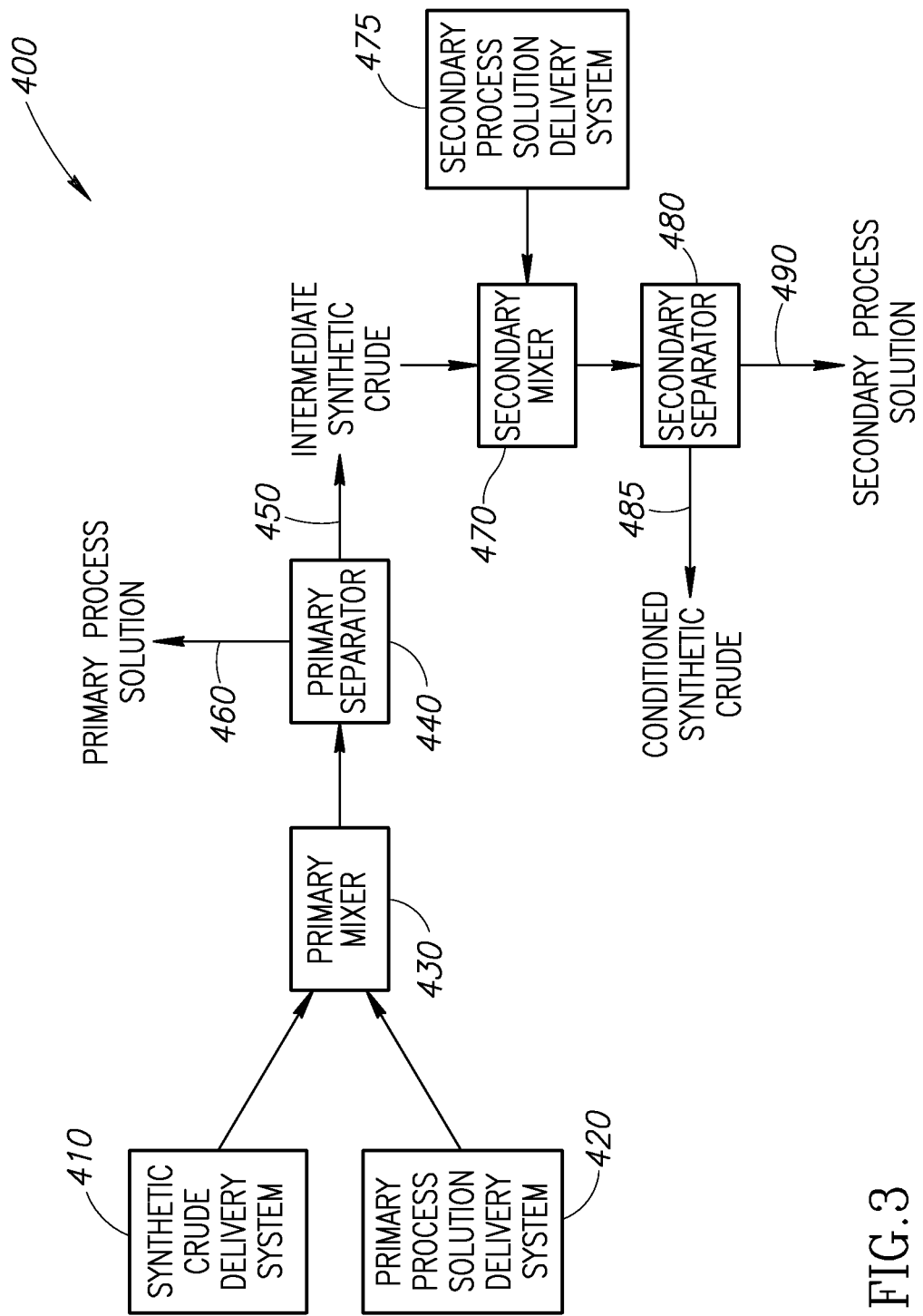
FIG. 3 provides a schematic illustration of an embodiment of a synthetic crude oil conditioning system configured for multiple conditioning steps.

FIG. 3 illustrates a conditioning system 400 configured to carry multiple conditioning and separation steps. Depending on the nature of the synthetic crude oil, it may be desirable to subject the synthetic crude to two or more conditioning steps. The conditioning system illustrated in FIG. 3 is configured to provide conditioning of a synthetic crude by a primary process solution and, subsequently, by a secondary process solution. Though the system illustrated in FIG. 3 is configured for a two-step conditioning process, it is to be understood that the systems described herein are not so limited. For example, the systems described herein can be configured for sequential conditioning of a synthetic crude oil by mixing the synthetic crude with three or more processing solutions.

In the embodiment illustrated in FIG. 3, the conditioning system 400 includes a synthetic crude delivery system 410, a primary process solution delivery system 420, a primary mixer 430, and a primary separator 440. The primary process solution may be formulated to target removal of one or more particulate, metal, metalloid, or alkaline contaminants. For instance, the primary process solution may be an acidic process solution and/or a chelating process solution.

An acidic process solution can include one or more chemical amendments of any suitable variety to achieve the desired properties, and the presence, combination, and/or concentration of one or more materials within an acidic process solution can be selected to remove targeted contaminants from the synthetic crude oil as it interacts with the acidic process solution. An acidic process solution may include strong and/or weak inorganic acids (e.g., hydrochloric acid, acetic acid) or one or more pH buffered solutions (e.g., acetic acid+sodium acetate). Where utilized, an acidic process solution with be formulated to exhibit a pH below about 7, with particular embodiments being formulated to exhibit a pH selected from less than about 6, less than about 5, less than about 4, and less than about 3. Washing synthetic crude oil with an acidic process solution may neutralize or remove alkaline chemical species. In doing so, a synthetic crude oil exhibiting a targeted alkalinity may be produced. In addition to reducing the alkalinity of a crude oil, an acidic process solution may serve to absorb organic acids, inorganic acids, metals, metalloids, certain polar organic molecules, and/or other impurities that have an affinity to or will partition with an acidic solution.

A chelating process solution may be formulated to remove metal or metalloid contaminants from a synthetic crude. Metals are one of the least desirable class of heteroatoms, as they can be particularly problematic to catalysts and other aspects of refining processes. In certain embodiments, a chelating agent is one that chelates, fixes, or otherwise binds one or more metal species and exhibits a tendency to partition into aqueous process solutions. An example of a chelating agent that may be incorporated into a chelating process solution is ethylenediaminetetraacetic acid (EDTA).

With continued reference to FIG. 3, mixing a synthetic crude with the primary process solution and separating the synthetic crude from the primary process solution using the primary separator 440 results in an intermediate synthetic crude oil 450. The intermediate synthetic crude oil 450 is then delivered to a secondary mixer 470 where it is blended with a secondary process solution 475. In the embodiment shown in FIG. 3, the secondary process solution is a caustic process solution as previously described herein. The blended intermediate synthetic crude oil 450 and the secondary process solution 475 are delivered to a secondary separator 480 which separates the secondary process solution 490 from the conditioned synthetic crude oil 485. By configuring the conditioning system 400 to provide a caustic processing solution as the secondary (and final) process solution, a conditioned synthetic oil exhibiting a desired TAN is delivered.

III. Methods for Conditioning Synthetic Crude Oil

Methods for conditioning synthetic crude oil are also provided. The methods described herein include obtaining a synthetic crude oil and processing the synthetic crude oil using a conditioning system according to the present description. As detailed herein the conditioning systems can be adapted for processing of synthetic crude oils obtained from a variety of different materials using different production processes. In particular embodiments, the methods described herein provide a synthetic crude oil exhibiting a TAN of about 0.5 mg/g KOH or less. In certain such embodiments, the conditioned synthetic crude exhibits a TAN of about 0.3 mg/g KOH or less, and in still further such embodiments, the conditioned synthetic crude exhibits a TAN of about 0.1 mg/g KOH or less.

In order to achieve a conditioned synthetic crude exhibiting a desired TAN without undesired saponification or formation of a stable emulsion, in certain embodiments, the methods described herein include mixing the synthetic crude oil with one or more caustic process solutions exhibiting a pH of no more than about 10. In certain such embodiments, the pH of any caustic process solution in contact with the synthetic crude oil is maintained between about 8.0 and about 10, and in still further such embodiments, the pH of any caustic process solution in contact with the synthetic crude oil is maintained between about 9.0 and about 10, such as, for example, about 9.5.

Alternatively, in certain embodiments, methods for achieving a synthetic crude exhibiting a desired TAN include controlling only the initial pH of the caustic process solution used in the systems described herein. In such embodiments, the initial pH of the caustic process solution is between about 8.0 and about 10, and in still further such embodiments, the initial pH of any caustic process solution in contact with the synthetic crude oil is between about 9.0 and about 10, such as, for example, about 9.5.

In order to achieve a conditioned synthetic crude exhibiting a desired TAN, methods according to the present description may also include determining the volume or flow rate of synthetic crude oil to be conditioned, calculating a volume or flow rate of caustic process solution required to maintain the pH of the process solution at a pH of between about 8.0 and about 10 once the process solution is mixed with the determined volume or flow rate of synthetic crude oil, and delivering the calculated volume or flow rate of caustic process solution to the determined volume or flow rate of crude oil. In this manner, the pH of the caustic process solution can be maintained at the desired alkalinity without increasing the pH of the caustic process solution above about 10. In specific embodiments, calculating the volume or flow rate of caustic process solution may include calculating the volume or flow rate of caustic process solution required to maintain the pH of the process solution at a pH of between about 9.0 and about 10, such as a pH of about 9.5, once the process solution is mixed with the determined volume or flow rate of synthetic crude oil. In embodiments of the methods described herein, the ratio of the volume of synthetic crude to the volume of process solution delivered to the mixer 230 may fall within a range selected from the group of ranges consisting of above about 1:1 to about 1:200, about 1:2 to about 1:200, about 1:3 to about 1:200, and about 1:4 to about 1:200. In further such embodiments, the ratio of the volume of synthetic crude to the volume of process solution delivered to the mixer 230 may be a range selected from the group of ranges consisting of about 1:2 to about 1:100, about 1:2 to about 1:50, about 1:2 to about 1:25, about 1:2 to about 1:10, and about 1:2 to about 1:5.

It will be understood by those having skill in the art that changes may be made to the details of the above-described embodiments without departing from the underlying principles presented herein. For example, any suitable combination of various embodiments, or the features thereof, is contemplated. Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

Similarly, it should be appreciated that in the description provided of the embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, inventive aspects lie in a combination of fewer than all features of any single foregoing disclosed embodiment. It will be apparent to those having skill in the art that changes may be made to the details of the above-described embodiments without departing from the underlying principles set forth herein.

The claims following this Detailed Description are hereby expressly incorporated into this Detailed Description, with each claim standing on its own as a separate embodiment. This disclosure includes all permutations of the independent claims with their dependent claims. Recitation in the claims of the term "first" with respect to a feature or element does not necessarily imply the existence of a second or additional such feature or element. Elements specifically recited in means-plus-function format, if any, are intended to be construed in accordance with 35 U.S.C. §112 ¶6. Embodiments of the invention in which an exclusive property or privilege is claimed are defined as follows.

The invention claimed is:

1. A system for conditioning synthetic crude oil, the system comprising:
   a synthetic crude oil delivery system including a source of synthetic crude oil obtained by pyrolysis of one or more materials selected from polymer, plastic, and rubber materials;
   a process solution delivery system configured to provide a caustic process solution having a pH of between about 8 and about 10;
   a mixer positioned downstream of the synthetic crude oil delivery system and the process solution delivery system to receive and mix a first volume of the synthetic crude oil with a second volume of the process solution, the first volume of the synthetic crude oil being less than the second volume of the process solution; and
   a separator positioned downstream of the mixer that receives the mixture of synthetic crude oil and process solution, wherein the separator is configured to provide separation of conditioned synthetic crude oil from the process solution.

2. The system of claim 1, wherein the process solution is aqueous solution comprising a soluble caustic selected from the group consisting of potassium hydroxide (KOH), calcium hydroxide (Ca(OH)$_2$), cesium hydroxide (CsOH), Barium hydroxide (Ba(OH)$_2$), sodium hydroxide (NaOH), strontium hydroxide (Sr(OH)$_2$), and lithium hydroxide (LiOH).

3. The system of claim 2, further comprising one or more pH sensors, wherein the pH sensors are positioned within the system to evaluate the pH of the process solution.

4. The system of claim 3, further comprising a caustic delivery system, wherein the caustic delivery system is configured to deliver additional caustic material to the process solution if the pH of the solution decreases below about 8.

5. The system of claim 4, wherein the one or more pH sensors are operatively associated with the caustic delivery system to assist in maintaining the PH of the process solution between about 8 and about 10.

6. The system of claim 1, wherein the separator comprises a separation tank including one or more diffuser assemblies and the mixture of synthetic crude oil and process solution are delivered to the separation tank through the one or more diffuser assemblies.

7. The system of claim 6, wherein the separator comprises a primary separation tank comprising one or more weirs.

8. The system of claim 7, wherein the separation tank comprises one or more diffuser assemblies and the mixture of synthetic crude oil and process solution are delivered to the primary separation tank through the one or more diffuser assemblies.

9. The system of claim 6, further comprising a process solution collection system configured to collect process solution separated from the synthetic crude oil.

10. The system of claim 9, wherein the process solution collection system comprises one or more pH sensors.

11. The system of claim 10, wherein the system further comprises a caustic delivery system and the one or more pH sensors are operatively associated with the caustic delivery system such that the caustic delivery system introduces additional caustic material into the separated process solution to bring the pH of the process solution up to a pH of between about 8 and about 10.

12. The system of claim 11, further comprising a synthetic crude flow rate monitor configured to assess the volume of synthetic crude oil delivered to the mixer.

13. The system of claim 12, further comprising a filtration system for removing solid particulates entrained within the synthetic crude oil, wherein the filtration system comprises filter media capable of capturing entrained particulates exhibiting a size selected from the group consisting of 500 µm or less, 200 µm or less, 100 µm or less, 50 µm or less, 25 µm or less, 10 µm or less, 5 µm or less, and 1 µm or less.

* * * * *